United States Patent [19]

Bartley et al.

[11] Patent Number: 4,687,877
[45] Date of Patent: Aug. 18, 1987

[54] PROCESS FOR DIMERIZATION

[75] Inventors: William J. Bartley, Charleston; Werner C. von Dohlen, deceased, late of Charleston, both of W. Va., by Helga E. von Dohlen, executrix

[73] Assignee: Union Carbide Corporation, Danbury, Conn.

[21] Appl. No.: 880,033

[22] Filed: Jun. 30, 1986

Related U.S. Application Data

[63] Continuation-in-part of Ser. No. 845,314, Mar. 28, 1986, abandoned.

[51] Int. Cl.$^4$ ............................................. L07C 2/24
[52] U.S. Cl. .................................. 585/516; 502/345; 585/530
[58] Field of Search ............... 502/345, 344; 585/516, 585/530

[56] References Cited

U.S. PATENT DOCUMENTS

| | | | |
|---|---|---|---|
| 3,175,020 | 3/1965 | Wilkes | 585/516 |
| 3,260,770 | 7/1966 | Hambling et al. | 585/516 |
| 3,755,491 | 8/1973 | Hashimoto | 585/516 |
| 3,950,450 | 4/1976 | Hashimoto et al. | 585/516 |
| 4,388,480 | 6/1983 | Imai et al. | 585/516 |
| 4,544,790 | 10/1985 | Drake | 585/530 |
| 4,595,787 | 6/1983 | Drake | 585/530 |

FOREIGN PATENT DOCUMENTS

| | | | |
|---|---|---|---|
| 0143334 | 6/1985 | European Pat. Off. | 585/516 |
| 4640249 | 10/1966 | Japan | 585/516 |
| 4702603 | 3/1968 | Japan | 585/516 |
| 5011881 | 3/1970 | Japan | 585/516 |
| 1221818 | 2/1971 | United Kingdom | 585/516 |

OTHER PUBLICATIONS

Wilkes, Proceedings of 7th World Petroleum Congress, vol. 5, 299–308 (1968).

*Primary Examiner*—Asok Pal
*Attorney, Agent, or Firm*—Saul R. Bresch

[57] ABSTRACT

A process for the dimerization of propylene or a $C_4$ olefin or the codimerization of ethylene with propylene or a $C_4$ olefin comprising passing the olefin(s) in contact with a catalyst comprising (a) elemental potassium and (b) elemental copper, and (c) an alpha-alumina support therefor, wherein:

(i) the potassium is present in the catalyst in an amount in the range of about 0.25 to about 30 percent by weight based on the weight of the catalyst;
(ii) the ratio of copper to potassium, by weight, is in the range of about 0.1 to one to about 5 to one; and
(iii) the process is carried out at a temperature in the range of about 75° C. to about 225° C. and at a pressure in the range of about atmospheric pressure to about 10,000 psig.

3 Claims, No Drawings

PROCESS FOR DIMERIZATION

This application is a continuation-in-part of application Ser. No. 845,314 filed on Mar. 28, 1986, now abandoned.

TECHNICAL FIELD

This invention relates to a process for the dimerization or codimerization of certain lower alkenes, and a catalyst therefor.

BACKGROUND ART

Sodium and potassium metals supported on potassium carbonate carriers are known to be effective catalysts for the dimerization of propylene to 4-methyl-1-pentene, which is a useful comonomer in polymer synthesis. The same catalysts are effective in codimerizations. Unsupported sodium and potassium catalysts, however, give unsatisfactory polymerization rates, have poor selectivities, or do not demonstrate adequate catalyst life. The sodium and potassium catalysts, which utilize potassium carbonate supports, give a better performance than the unsupported metals, but have poor strength and are subject to undesirable attrition and the generation of fines during use and handling. These deficiencies result in poor economics due to catalyst losses and excessive pressure drops in the reactor.

DISCLOSURE OF INVENTION

An object of this invention, therefore, is to provide a dimerization/codimerization process and catalyst with which rates, selectivities, and catalyst life and strength are improved.

Other objects and advantages will become apparent hereinafter.

According to the present invention, a process has been discovered for the dimerization of propylene or a $C_4$ olefin or the codimerization of ethylene with propylene or a $C_4$ olefin comprising passing the olefin(s) in contact with a catalyst comprising (a) elemental potassium and (b) elemental copper, and (c) an alpha-alumina support therefor, wherein:

(i) the potassium is present in the catalyst in an amount in the range of about 0.25 to about 30 percent by weight based on the weight of the catalyst;

(ii) the ratio of copper to potassium, by weight, is in the range of about 0.1 to one to about 5 to one; and (iii) the process is carried out at a temperature in the range of about 75° C. to about 225° C. and at a pressure in the range of about atmospheric pressure to 10,000 psig.

DETAILED DESCRIPTION

In order to produce low density polyethylene in the low pressure process, an alpha-olefin is copolymerized with ethylene to provide the necessary short-chain branches. In certain areas of the world, 1-butene, which is presently the principal comonomer in the low pressure process, is not likely to be available at the low prices prevailing in the United States, Western Europe, and Japan. Alternatives universally available at these low prices, are being sought, and one alternative is 4-methyl-1-pentene. It appears to be the only $C_6$ alpha-olefin, which can be made with a reasonably high selectivity, i.e., up to 80 to 90 percent by weight of the propylene consumed. Alkali metal catalysts have been selected for this task even though the rates for alkali metal catalyzed oligomerization are, in general, lower by a factor of 10 to 100 than those catalyzed by transition metal catalysts. The reason for the selection is that propylene is not usually reactive with the transition metal complexes used to dimerize ethylene.

In addition to 4-methyl-1-pentene, subject process and catalyst can be advantageously used to produce 1-pentene, which is also useful as a comonomer in the low pressure process, and a mixture of $C_6$ olefins.

These products are produced by (i) the dimerization of propylene or a $C_4$ olefin or (ii) the codimerization of ethylene with propylene or a $C_4$ olefin. The $C_4$ olefins include 1-butene, 2-butene (cis), 2-butene (trans), and isobutylene.

Oligomerization rate (in subject process, dimerization or codimerization rate), rate, productivity, activity, and reactivity are synonymous in the context of this specification in that they are all measured by the number of grams of, for example, 4-methyl-1-pentene produced per gram of potassium utilized in the catalyst per hour (g/gK/hr).

Subject process may be carried out either in a batch mode or continuously using either liquid-phase or gas-phase conditions. While the process is particularly suited to continuous, fixed-bed operation, other variations, such as trickle-bed or a slurried batch operation, can be used. Standard tubular reactors and autoclaves can be employed with no special materials of construction being required. If the process is carried out in the liquid phase, it is preferable to use a solvent or diluent. Any saturated hydrocarbon or aromatic solvent, which is inert to potassium at reaction conditions, can be employed for this purpose.

Process temperatures can range from about 75° C. to about 225° C. with the range of about 100° C. to about 200° C. being preferred and the range of about 125° C. to about 180° C. being most preferable. Lower temperatures produce low activity and poor conversion and higher temperatures lead to decomposition products and short catalyst life, e.g., the production of black, solid, potassium-containing residues which can cause catalyst deactivation. Increasing temperature within the range produces dimerization rate increases.

The reaction rate increases with increasing pressure and, in general, pressures may be varied over a wide range, i.e., from atmospheric to about 10,000 psig. Pressures in the range of about 500 to about 5000 psig are preferred with pressures in the range of about 800 psig to about 1500 psig being considered optimum. Dropping the pressure results in a reduction of rate, e.g., from 1500 psig to 500 psig results in a reduction of rate to about one half of the rate obtained at 1500 psig. The effect on selectivity is minimal, however.

The contact time necessary to effect the reaction varies with the reaction conditions, the catalyst concentration, the reactivity of the olefin(s) being dimerized or codimerized, the conversion desired, and other process factors. Suitable contact times will, therefore, vary over a broad range, e.g., from a fraction of a second to many hours, with about 10 seconds to about 5 hours being preferred.

When operating in a continuous, fixed-bed mode with a liquid olefin, it is convenient to specify contact times in terms of the liquid hourly space velocity (LHSV), which is defined as the volume of liquid olefin fed per hour per unit volume of catalyst. Space velocities can be varied over a relatively wide range, i.e., from about 0.25 to about 10. A more preferred LHSV range is from about 0.5 to about 4 with about 1 to about 3 being most preferred. In general, lower LHSV's give higher conversions and poorer selectivities. Higher LHSV's give the highest selectivities, but are generally less economical because the resultant low conversions necessitate the recycle of large amounts of unreacted olefin. Gas hourly space velocities are used in the case of gaseous feeds. Criteria similar to those for liquids apply.

The catalyst is made up of three components: (a) elemental potassium; (b) elemental copper; and (c) an alpha-alumina support therefor.

The support preferably has an acidity of no greater than about 0.5 microgram per gram of support as determined by the absorption of pyridine vapor.

The determination of acidity by the absorption of pyridine vapor is accomplished as follows:

(i) A dilute mixture of amine in helium is generated by bubbling helium through a glass saturator, which is maintained at 0° C. by immersing in a Dewar flask filled with ice water. The partial pressure of amine is given by its vapor pressure at 0° C. A sample is placed in a quartz U-tube contained in a sand bath. For materials with high acidity, a 1.5 cubic centimeter (cc) sample in a tube with a 3 millimeter (mm) internal diameter (i.d.) is used. For materials with low acidity, a 4.5 or 6.0 cc sample in an 8 mm i.d. tube is used. The sand is fluidized with air and heated using a proportional temperature controller, F & M Model 220. The helium flow either through or bypassing the amine saturator and the sample U-tube is controlled independently by means of a series of three-way valves.

(ii) The presence of amine in the helium is detected by a F & M Model 720 gas chromatograph equipped with a thermal conductivity detector. The chromatograph is operated with a blank column under the following conditions:

oven: room temperature
detector block: 235° C.
injection: 190° C.
bridge current: 150 milliamps
helium flow: 37.5 cc/minute The amine is reagent grade pyridine or 2,6-dimethyl-pyridine, which are redistilled prior to use.

(iii) The sample is charged to the quartz U-tube and helium flow is started through the tube with the amine saturator being bypassed. The sample is heated to 500° C., usually taking three hours, held there for two hours to drive off all sorbed water, and then cooled to 400° C. for the measurement. Before the determination is made, the sample tube is bypassed and the saturator is purged with helium for 15 minutes to remove any air that has leaked in. The saturator is then bypassed. After the amine has been swept from the system, the sample tube is opened and the gas chromatograph is allowed to stabilize from the flow upset caused by switching valves. The saturator is then opened and the amine breakthrough time (B.T. #1) is recorded. This gives combined physical and chemical adsorption. The saturator is then bypassed and helium is passed through the sample for 30 minutes to drive off physisorbed amine. The saturator is opened again and the amine breakthrough time (B.T. #2) is recorded. This gives the quantity of physisorbed amine. System "dead volume" is determined by measuring the amine breakthrough time with an equivalent volume of quartz chips in place of the sample (B.T.: quartz chips).

An acidity of no greater than about 0.2 microgram per gram of support is even more preferable. Essentially no acidity would, of course, be optimum.

The surface area of the support selected is at a level which will not raise the acidity above the prescribed upper limit. Subject to this proviso, the surface area can be in the range of about 0.2 square meter per gram to about 40 square meters per gram and is preferably in the range of about 0.5 square meter per gram to about 5 square meters per gram. It will be understood that the greater the surface area, the greater the number of acidic sites and, therefore, the greater the acidity. However, the acidity of high surface area supports can frequently be reduced to acceptable limits by, for example, the use of basic oxide additives, high temperature treatment, removal of acidic impurities, and surface passivation.

Finally, the support is one which is essentially inert insofar as process components and conditions, e.g., the olefins, potassium, copper, process temperature, and process pressure, are concerned.

The alpha-alumina support contemplated here is found to be superior to potassium carbonate supports in that the alpha-alumina support has superior mechanical strength and durability; an insignificant number of fines are produced under reaction conditions; and an increase in dimerization or codimerization rates is observed. The alpha-alumina support can also provide varied physical properties in a variety of sizes and shapes. This variety aids in tailoring catalysts with (i) reduced diffusional resistance within the catalyst pellet and (ii) low pressure drop when used in fixed-bed reactors. Further, catalyst manufacture with alpha-alumina does not require a separate pelletizing step, which is necessary with potassium carbonate and many other supports. In lieu of alpha-alumina, a robust support meeting the requirements mentioned above should be selected.

The concentration of potassium used in subject catalyst can be in the range of about 0.25 to about 30 percent by weight based on the weight of the catalyst, and is preferably in the range of about 1 to about 10 percent. The range of about 2 to about 5 percent is most preferred. Productivity increases with increased potassium loading, but selectivity tends to decrease. At high loadings, metal agglomeration becomes excessive and the effectiveness of the catalyst is reduced. Very low loadings result in low reaction rates and poor process economics. It is observed that low potassium loadings require very large reactor volumes to obtain a commercially satisfactory 4-methyl-1-pentene output.

Copper is preferably applied to the support and reduced to the elemental metal prior to the addition of the potassium. The copper can be deposited on the support in the form of a copper salt dissolved in water, ammonia, or a non-aqueous solvent such as methanol or ethanol. Conventional calcining/reduction steps and conditions can be followed. Hydrogen is the preferred reducing agent, but other reducing agents such as carbon monoxide or hydrazine can be employed. If desired, potassium metal can be used to effect the reduction of the copper at the time of potassium application, but it should be recognized that an equivalent portion of this potassium will no longer be catalytically active due to its conversion to oxide. The weight ratio of copper to potassium can be in the range of about 0.1 to one to about 5 to one and is preferably in the range of about 0.5 to one to about 3 to one. Further, the copper/potassium weight ratio is preferably increased as the weight percent of potassium in the catalyst is increased. For example, optimum results with catalysts containing about 2 percent potassium are obtained with a copper/potassium weight ratio of about 1:1 whereas with 5 percent potassium catalysts, copper/potassium ratios of about 2:1 are required to get optimum results.

In any case, it should be noted that subject catalysts can take several days to reach peak performance, and, after a period of peak performance, may show a decline. It is also observed that better selectivities are obtained in single pass tubular reactors. The use of promoters such as butanol is optional.

Selectivity drops at higher conversions due to isomerization to internal olefins. There is an indication, however, that at conversions above 15 percent by weight based on the olefin reacted, the effect of conversion on selectivity is of decreasing importance.

The invention is illustrated by the following examples. Percentages are by weight unless otherwise stated.

EXAMPLE I

All reagents and reaction vessels are thoroughly dried. Alpha-alumina is dried under a dinitrogen flow at 400° C. for 3 to 4 hours. The alpha-alumina support is then impregnated with an ethanolic solution of copper (II) acetate hydrate, which is then reduced in dihydrogen and dinitrogen (200 cc + 200 cc, respectively, per minute) at 230° C. for 1 hour and, then, 350° C. for 2 hours. Potassium is added after the reduction by agitating the alpha-alumina in a calculated quantity of liquid metal at 130° C. The potassium addition and all subsequent handling is performed in an inert atmosphere.

Product analysis is performed by isothermal gas chromatography at 40° C. using a 20-foot by ⅛-inch gas chromatograph stainless steel column packed with 60 to 80 mesh Chromosorb P coated with 20 percent by weight (based on the weight of the Chromosorb P) tributyl phosphate operated isothermally at 40° C. A thermal conductivity detector is used with 20 cubic centimeters per minute helium flow. Absolute calibrations are not performed, and area percent is assumed equal to weight percent, which is believed to be accurate to 10 to 15 percent.

Runs are made in the vapor phase in a tubular reactor with propylene being fed as a liquid using a conventional reaction system, except that in runs 5 and 6, a mixture of propylene and ethylene are introduced into the system in a ratio of 1:1. The product in runs 5 and 6 is 1-pentene. Small amounts of 4-methyl-1-pentene are also observed.

The tubular reactor is a 36 inch by 1 inch Schedule 80 stainless steel tube fitted with a ¼ inch thermowell extending up from the bottom of the tube for three quarters of the length of the reactor. A glass wool plug is installed near the bottom to support the catalyst. The tube is heated and purged with nitrogen to dry the glass wool plug, then cooled. 180 cubic centimeters of catalyst are introduced into the tube with a funnel in a plastic glove bag under a nitrogen purge (a slow purge up the tube and a rapid purge in the bag).

The top of the catalyst bed is determined and thermocouples are placed at two inch intervals from the top of the bed to the bottom of the bed. The heated portion of the tube above the catalyst bed serves as the preheater. Liquid propylene is pumped from a reservoir to build system pressure to the desired level usually 1500 pounds per square inch gauge (psig). 800 psig is employed for the ethylene/propylene equimolar feed. The system is slowly heated to 140° to 180° C. and 2 to 3 hour timed runs are made. The uncondensed product gas is analyzed at regular intervals by on-line gas chromatography. Liquid products collected in the product receiver are drained periodically.

The variables and results are set forth in Table I.

In Table I: percent K and Cu are based on the combined weight of the catalyst components inclusive of the support. LHSV is given in hours to the minus one power ($hr^{-1}$). Conversion is the percentage of the propylene or ethylene/propylene introduced into the reactor which is converted to 4-methyl-1-pentene or 1-pentene. Selectivity is the percentage of 4-methyl-1-pentene or 1-pentene relative to total product. Rate is, as noted above, the dimerization rate in terms of grams of 4-methyl-1-pentene produced per gram of potassium used per hour or, in the case of ethylene/propylene feed, the grams of 1-pentene per gram of potassium used per hour.

TABLE I

| Run | K (percent) | Cu (percent) | temperature (°C.) | pressure (psig) | LHSV ($hr^{-1}$) | conversion (percent) | selectivity (percent) | rate (g/gK/hr) |
|---|---|---|---|---|---|---|---|---|
| 1 | 11.8 | 1.9 | 160 | 1500 | 1 | 41 | 82 | 3.1 |
| 2 | 11.8 | 1.9 | 160 | 1500 | 2 | 27 | 85 | 4.2 |
| 3 | 11.8 | 1.9 | 180 | 1500 | 1 | 47 | 80 | 3.4 |
| 4 | 11.8 | 1.9 | 180 | 1500 | 2 | 41 | 77 | 5.8 |
| 5 | 11.8 | 1.9 | 150 to 155 | 800 | 2 | 8 | 79 | 1.2 |
| 6 | 11.8 | 1.9 | 146 to 181 | 800 | 1 | 22 | 73 | 1.2 |
| 7 | 2.0 | 2.0 | 130 | 500 | 1.25 480* | 16.0 12.3** | 88 | 11.6 |
| 8 | 2.0 | 5.0 | 120 | 500 | 1.46 480* | 11.0 10.7** | 87 | 9.3 |
| 9 | 2.0 | 3.3 | 119 | 500 | 1.81 533* | 11.2 9.0** | 90 | 11.0 |

*The top number is the LSHV ($hr^{-1}$) for propylene. The bottom number is the GHSV ($hr^{-1}$) for ethylene. This is the gas hourly space velocity defined as the volume of gaseous olefin, i.e., ethylene, fed per hour per unit volume of catalyst.
**The top number is the conversion (percent) for propylene. The bottom number is the conversion (percent) for ethylene.

EXAMPLE II

Vapor phase propylene dimerization is carried out in the continuous mode using a conventional reaction system.

Variables and results are set forth in Table II.

The alpha-alumina support has a surface area of about 0.5 square meters per gram. The acidity is no greater than about 0.5 microgram per gram of support (as determined by the absorption of pyridine vapor). Any alpha-alumina which meets the acidity criteria can be used. The supports used here are purchased from the Norton Company. One is designated as SA 5536 and has a purity of 98.5 percent and another is designated as 82185 and has a purity of 99.9 percent. Differences in performance are found to be insignificant. All of the runs are with SA 5536, except run 15, which is with 82185.

The catalyst is prepared as follows: alpha-alumina, broken and sized to 6 to 16 mesh, is weighed in a porcelain evaporating dish. The quantity of copper acetate required for the desired weight percent copper in the finished catalyst is dissolved in a minimum of boiling water, and an aliquot of the hot solution, which is just sufficient to wet the alumina, is added. The damp mixture is warmed with frequent stirring using a heat lamp located about 15 inches above the dish until most of the excess moisture evaporates. More copper acetate is added, and the process repeated until all of the copper acetate is deposited (3 to 5-hour total evaporation time). The dried carrier is calcined in air at 400° C. for 3.5 to 4 hours, then transferred quickly to a 250 milliliter, four necked flask, which is equipped with an oil-sealed, glass paddle stirrer; a thermocouple; an inlet for hydrogen, nitrogen, or argon; and an outlet tube to a mineral oil bubbler. The system is purged with nitrogen for 1 hour while heating to about 140° C., after which hydrogen is introduced into the nitrogen stream giving a final concentration of 1 to 2 percent. After 4 to 5 hours at these conditions with occasional stirring, the flask is further warmed to about 170° C. and held at this temperature overnight. A final heating at 200° C. for 1 hour is used to assure complete reduction. The flask is then cooled while purging with dry, oxygen-free argon. Potassium metal is cut under heptane, surface oxide is removed by a short immersion in 5/1 n-heptane/n-propanol, and the required quantity of potassium is weighed under fresh heptane. The potassium is quickly transferred to the flask, and the system is again purged with argon. The contents of the flask are warmed slowly to about 80° C. to melt the potassium, while stirring the mixture by hand using the paddle stirrer. Metal distribution is poor at this stage, but improves substantially by heating and stirring to a final temperature of about 230° C. The mixture is allowed to stand with intermittent stirring at this final temperature for one hour, and is then cooled under argon. The catalyst is transferred to a dry, argon-purged bottle using a well-purged (argon) glove bag, and the cap is sealed from air and moisture with molten paraffin wax.

The catalyst is tested in a tubular reactor (one-inch diameter × 11/16-inch inner diameter × 18 inches long, and fitted with an annular, ⅛-inch thermocouple well), which is dried and purged with a stream of nitrogen. A bed of dry silica chips (about 15 milliliters deep) is added as an inert filler, and a nitrogen purged glove bag containing the bottled catalyst and a funnel is attached to the top of the reactor. The catalyst (about 25 to 50 milliliters) is added to the reactor with the aid of the funnel under a nitrogen atmosphere and a second layer of silica chips is added to fill the remaining portion of the reactor. The reactor is sealed and thermocouples are inserted to points at the top, center, and bottom of the catalyst bed. A preheater/deoxygenator, which is packed with 2.5 liters of activated copper chromite/silica catalyst is heated to a temperature in the range of about 140° C. to about 150° C., and heat tapes between the preheater and the reactor and the steam tracings on the reactor exit lines are heated to a temperature in the range of about 120° C. to about 150° C. Liquid propylene is pumped from a reservoir to the preheater and reactor to build the system pressure to the desired level, usually 1500 psig. Then the catalyst is heated to about 100° C. When a propylene purge through the system is verified, the reactor is slowly warmed to the desired operating temperature, and 2 to 3 hour timed runs are initiated. The uncondensed product gas is analyzed at regular intervals by on-line gas chromatography using the system and procedure outlined below. Liquid products collected in the product receiver are drained periodically, but are not routinely analyzed.

The product stream is analyzed by gas chromatography using a chromatograph equipped with a flame ionization detector, a 60-meter × 0.25-millimeter internal diameter capillary column (J & W Scientific, DB-5 Silicone), and an oven temperature of 30° C. The chromatograph is calibrated using the external standard technique. Typical product distributions and retention times are as follows:

| component | retention time (in minutes) | mole percent |
|---|---|---|
| propylene | 5.3 | 91.5 |
| 4-methyl-1-pentene | 11.9 | 8.0 |
| cis-4-methyl-2-pentene | 12.7 | 0.08 |
| trans-4-methyl-2-pentene | 12.9 | 0.37 |
| 1-hexene | 14.5 | 0.53 |
| cis and trans-2- and/or 3-hexenes | 16.3 | 0.08 |
| 2-methyl-2-pentene | 17.4 | 0.05 |

In Table II:

1. Percent of K and Cu are based on the combined weight of the catalyst components inclusive of the support.
2. The catalyst volume is given in milliliters.
3. The hours represent the total reaction time with a given catalyst.
4. The temperature is the peak temperature in the reactor.
5. The pressure is the reaction pressure.
6. Percent conversion is the percent of propylene introduced into the reactor which is converted to 4-methyl-1-pentene.
7. The rate is grams of 4-methyl-1-pentene produced per gram of potassium per hour.
8. The selectivity is measured at about 10 percent conversion, and is based on the percent of 4-methyl-1-pentene in the total product.
9. A = 4-methyl-1-pentene; B = cis-4-methyl-2-pentene; C = trans-4-methyl-2-pentene; and D = 1-hexene.

TABLE II

| Run | K (percent) | Cu (percent) | catalyst (ml) | hours | temp. (°C.) | psig | percent conversion | rate (g/gK/hr) | Selectivity (percent) A | B | C | D |
|---|---|---|---|---|---|---|---|---|---|---|---|---|
| 1 | 2 | 1 | 50 | 218 | 150 | 1500 | 13.0 | 6.4 | 89.0 | 0.8 | 3.5 | 5.6 |
| 2 | 2 | 2 | 50 | 52 | 150 | 1500 | 11.8 | 4.8 | 89.2 | 1.6 | 2.9 | 5.4 |
| 3 | 2 | 2 | 50 | 25 | 150 | 1500 | 12.8 | 7.8 | 89.1 | 0.8 | 3.5 | 5.4 |
| 4 | 2 | 2 | 50 | 52 | 150 | 1500 | 14.2 | 6.9 | 88.9 | 0.8 | 3.7 | 5.4 |
| 5 | 2 | 2 | 50 | 199 | 150 | 1500 | 14.5 | 10.0 | 88.2 | 0.7 | 4.8 | 5.1 |

TABLE II-continued

| Run | K (percent) | Cu (percent) | catalyst (ml) | hours | temp. (°C.) | psig | percent conversion | rate (g/gK/hr) | Selectivity (percent) A | B | C | D |
|---|---|---|---|---|---|---|---|---|---|---|---|---|
| 6 | 2 | 3.3 | 50 | 195 | 150 | 1500 | 10.3 | 5.9 | 90.4 | 0.9 | 3.7 | 4.9 |
| 7 | 2 | 3.3 | 45 | 217 | 150 | 1500 | 10.3 | 7.4 | 90.6 | 0.8 | 3.3 | 5.2 |
| 8 | 2 | 5 | 50 | 79 | 150 | 1500 | 10.5 | 4.8 | 90.9 | 0.5 | 3.6 | 4.6 |
| 9 | 2 | 5 | 50 | 170 | 150 | 1500 | 13.7 | 8.2 | 87.9 | 0.8 | 3.8 | 6.2 |
| 10 | 5 | 2.5 | 50 | 173 | 150 | 1500 | 10.6 | 6.0 | 84.5 | 1.6 | 6.8 | 5.6 |
| 11 | 5 | 5 | 25 | 223 | 150 | 1500 | 17.4 | 6.3 | 87.8 | 1.1 | 5.1 | 4.9 |
| 12 | 5 | 5 | 25 | 152 | 150 | 1500 | 9.1 | 6.2 | 88.7 | 0.8 | 4.1 | 5.6 |
| 13 | 5 | 5 | 30 | 198 | 150 | 1500 | 12.3 | 5.6 | 88.0 | 1.3 | 4.6 | 5.4 |
| 14 | 5 | 10 | 25 | 199 | 150 | 1500 | 10.5 | 7.4 | 88.9 | 1.0 | 4.7 | 5.4 |
| 15 | 10 | 2 | 50 | 80 | 138 | 1500 | 18.0 | 3.1 | 83.0 | 2.1 | 8.5 | 4.7 |
| 16 | 10 | 5 | 8 | 103 | 150 | 1500 | 5.5 | 3.3 | 86.9 | 0.9 | 4.9 | 6.2 |
| 17 | 10 | 10 | 10 | 99 | 150 | 1500 | 10.3 | 4.5 | 83.7 | 1.3 | 7.6 | 5.5 |
| 18 | 2 | 2 | — | — | 150 | 1500 | 8.2 | 7.2 | 88 | — | — | — |

We claim:

1. A process for the dimerization of propylene or a C$_4$ olefin or the codimerization of ethylene with propylene or a C$_4$ olefin comprising passing the olefins(s) in contact with a catalyst comprising (a) elemental potassium and (b) elemental copper, and (c) an alpha-alumina support therefor, wherein:
   (i) the potassium is present in the catalyst in an amount in the range of about 2 to about 5 percent by weight based on the weight of the catalyst;
   (ii) the ratio of copper to potassium, by weight, is in the range of about 0.1 to one to about 5 to one;
   (iii) the surface area of the support is in the range of about 0.2 square meters per gram to about 5 square meters per gram; and
   (iv) the process is carried out in the gas phase at a temperature in the range of about 75° C. to about 225° C. and at a pressure in the range of about atmospheric pressure to about 10,000 psig.

2. The process defined in claim 1 wherein the ratio of copper to potassium is in the range of about 0.5 to one to about 3 to one.

3. The process defined in claim 1 wherein the temperature is in the range of about 100° C. to about 200° C. and the pressure is in the range of about 500 psig to about 5000 psig.

* * * * *